(12) United States Patent
Walter

(10) Patent No.: US 6,720,417 B1
(45) Date of Patent: Apr. 13, 2004

(54) METHOD AND DEVICE FOR REFINING NUCLEIC ACIDS

(75) Inventor: Thomas Walter, Penzberg (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/355,365

(22) PCT Filed: Jan. 26, 1998

(86) PCT No.: PCT/EP98/00408

§ 371 (c)(1),
(2), (4) Date: Nov. 19, 1999

(87) PCT Pub. No.: WO98/32877

PCT Pub. Date: Jul. 30, 1998

(30) Foreign Application Priority Data

Jan. 28, 1997 (DE) .......................... 197 02 907

(51) Int. Cl.⁷ ............................... C07H 21/00
(52) U.S. Cl. ....................................... 536/25.4
(58) Field of Search ................ 270/679; 536/25.4; 435/6

(56) References Cited

U.S. PATENT DOCUMENTS

| | | | | |
|---|---|---|---|---|
| 5,438,128 A | | 8/1995 | Nieuwkerk et al. | ......... 536/25.4 |
| 5,910,246 A | * | 6/1999 | Walter et al. | ................ 210/232 |
| 6,017,698 A | * | 1/2000 | Bienhaus et al. | ............... 435/6 |
| 6,090,936 A | * | 7/2000 | Walter et al. | ............... 536/25.4 |
| 6,264,814 B1 | * | 7/2001 | Lange | ........................ 204/450 |

FOREIGN PATENT DOCUMENTS

| | | | |
|---|---|---|---|
| DE | 195 12 369 A1 | | 10/1996 |
| DE | 197 02 907.8 | * | 1/1997 |
| EP | 0 734 768 A1 | | 2/1996 |
| WO | WO 91/07648 | | 5/1991 |
| WO | WO 95/06652 | | 3/1995 |
| WO | WO 95/27546 | | 10/1995 |
| WO | WO 96/06850 | | 3/1996 |
| WO | WO 97/21484 | | 6/1997 |
| WO | WO98/32877 A1 | * | 7/1998 |
| WO | WO99/13976 A1 | * | 3/1999 |

OTHER PUBLICATIONS

S. A. Miller, et al., "A simple salting out procedure for extracting DNA from human nucleated cells," Nucleic Acids Research, 16:1215 (1988).

Vogelstein, et al., "Preparative and analytical purification of DNA from agarose," Proc. Natl. Acad. Sci. USA, 76:615–619 (1979) (Feb., 1979).

* cited by examiner

*Primary Examiner*—James O. Wilson
*Assistant Examiner*—L. E. Crane
(74) *Attorney, Agent, or Firm*—Marilyn Amick; Roche Diagnostics Corporation

(57) ABSTRACT

A device for isolating nucleic acids which reduces the transfer of contaminants during nucleic acid isolation methods which is composed of two vessels which are linked by a closing element in which a material that binds nucleic acids is placed. The nucleic acid can for example be bound to the material by tipping the device.

11 Claims, 2 Drawing Sheets

Figure 1C:
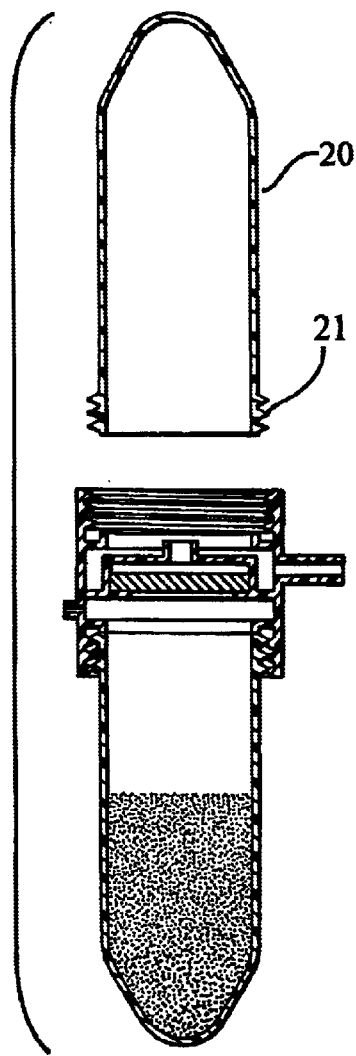

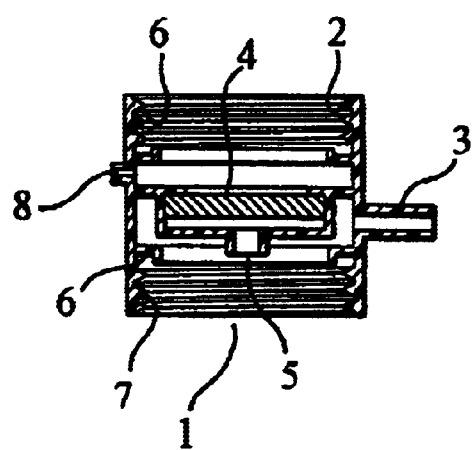
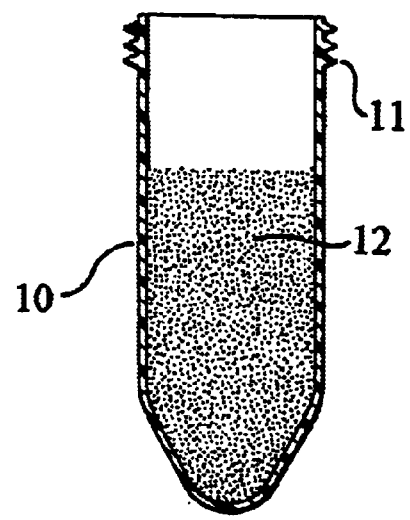
FIG. 1A
FIG. 1B

METHOD AND DEVICE FOR REFINING NUCLEIC ACIDS

The invention concerns a method for the isolation of nucleic acids from a sample and a suitable device for this.

The introduction of the polymerase chain reaction (PCR) and subsequent alternative amplification systems for nucleic acids enabled this genetic material to be used as a material for examination by diagnostic tests. This has resulted in new analytical opportunities above all for the diagnosis of hereditary diseases, predisposition for certain diseases and infectious diseases which, among others, allows an earlier detection of the condition.

In order to convert the genetic material into a suitable form for enzymatic amplification, it is always necessary to release it from the biological sample material. In addition the nucleic acid must be protected from degradation by nucleases in the biological material or the environment and from degradation by chemical reaction conditions ($Fe^{++}$/DTT or $\beta$-mercaptoethanol; NaOH; heat). The greatest demands are made on the freedom from contamination of the biological sample and of the nucleic acid that is isolated from it. In particular it is necessary to prevent transfer from the environment, by laboratory staff and cross-contamination between samples. The nucleic acid should be present in a buffered, aqueous, substantially salt-free solution for the amplification.

Whereas PCR always uses very small amounts of analyte (pg/ng range), special problems may require the processing of a larger amount of sample. In order to, for example, identify circulating tumour cells with a sensitivity of one tumour cell in a background of $10^7$–$10^8$ normal cells, the nucleic acid must for example be isolated from 10–20 ml of a blood sample. After homogenizing the sample, an aliquot of the isolated RNA can thus be examined for expression of a tumour-associated gene.

In addition to the classical methods of nucleic acid isolation by means of enzymatic, mechanical or chemical lysis of the sample material, subsequent extraction of the proteins and lipids by phenol and phenol/$CHCl_3$ and precipitation of the nucleic acid from the aqueous phase with ethanol or i-propanol (Sambrook, J., Fritsch E. F. and T. Maniatis Molecular Cloning, Cold Spring Harbor Laboratory Press, 1989, 2nd edition, 9.16–9.23; Ausubel F. M. et al. Current Protocols in Molecular Biology, John Wiley & Sons, 1987, 2.1.1–2.4.5), several commercial kits have been developed in recent years especially for PCR sample preparation which utilize the property that nucleic acids bind to glass surfaces under chaotropic salt conditions which has been known since the end of the seventies (Vogelstein B. et al., Proc.Natl.Acad.Sci: USA, 76 pp 615–619 (1979)). Other constituents of biological material such as proteins, lipids or salts are not bound and are therefore separated. Centrifugation vessels with glass fleece inserts for sample volumes up to 200 $\mu$l or silica gel suspensions which allow a batch process are known. Furthermore multiple devices in a strip and 96-well microtitre plate format with glass fleeces inserted in the bottom are known which can be operated with the aid of a vacuum chamber that is mounted underneath as well as by centrifugation. In these methods there is a great risk of contamination since all the vessels are in contact via the airspace with vacuum suction as well as with centrifugation and contamination by aerosols can occur.

A modified method (Miller et al., Nucl. Acids Res. 16: 1215) uses a concentrated salt solution to precipitate proteins and other accompanying substances after lysing the sample material. The nucleic acids in the supernatant are then precipitated by ethanol and collected by centrifugation. After the nucleic acids have been dissolved, they can be used for the amplification.

The current approaches are either limited with regard to the size of the volume that can be processed or are more time consuming or require an additional step to precipitate the nucleic acids. A multiple application is time consuming and increases the risk of contamination and mistakes. Batch process can be fundamentally scaled up but even then they have a risk of contamination.

Hence the object of the present invention was to provide a simple method for isolating nucleic acids from larger sample volumes.

Hence the invention concerns a method for isolating nucleic acids from a sample by taking the sample up into a first vessel through an opening, closing the opening of the first vessel with a closing element which contains a nucleic-acid-binding, liquid-permeable material and which on the side facing the opening contains means for attaching the element on the first vessel and, on the other side of the material, contains means for attaching the element to a second vessel, and transferring the sample through the material into the vessel attached to the other side. The invention also concerns a device for carrying out this method.

The components of the device according to the invention and the individual phases of the method according to the invention are shown schematically and as an example in FIG. 1.

A method for isolating nucleic acids is understood as a method in which nucleic acids in a sample are separated from other sample components. This is achieved by binding the nucleic acids to a nucleic-acid-binding material. After the binding, the liquid can be separated from the material containing the nucleic acids. In order to isolate particularly pure nucleic acids, it is possible to remove substances that may still be adhering by washing the material with a liquid. If desired the nucleic acids can be detached again from the nucleic-acid-binding material. The nucleic acids are bound or detached from the material under conditions that depend on the material used.

Nucleic-acid-binding materials are known to a person skilled in the art. The material can be particulate and also fibrous. If the material is composed of particles it has proven to be advantageous to immobilize these particles e.g. by placing them between small liquid-permeable plates e.g. fabrics or fleeces made of fibrous material such as cellulose or plastics which have such narrow pores that the particles are held between the plates. However, the nucleic-acid-binding material is preferably a fibrous material e.g. in the form of fabrics or fleeces. Suitable materials are for example known from methods for isolating nucleic acids with the aid of centrifugation tubes or multiple devices in a strip format. The nucleic-acid-binding material must have the property that the sample liquid can pass through the material without any additional action of force or by applying a force e.g. by applying pressure or underpressure. However, since in the present method the nucleic acids are not bound by filtration of the nucleic acids from the sample, but by a method which utilizes the affinity of nucleic acids for surfaces, it is possible to use a relatively coarse porous material. This facilitates the flow even of relatively viscous sample liquids.

The liquid-permeable material is able to bind nucleic acids but allows passage of other components dissolved therein such as proteins etc. In a first variant the nucleic acids can be bound sequence-specifically by capture probes attached to the surface of the material. The capture probes have a base sequence which can bind under hybridization conditions to a complementary base sequence in the nucleic acids to be isolated. The use of sequence-specific materials allows the selective isolation of nucleic acids having a particular sequence. A method for binding nucleic acids to peptidic nucleic acids on the surface of solids is described for example in WO 95/14708. In a preferred case the liquid-permeable material has a glass-containing surface. The property of being able to bind nucleic acids has been already known for a long time for particulate and fibrous materials. Thus the use of glass fleeces for isolating nucleic acids is described for example in DE-A-19512369.

Nucleic acids within the sense of the invention are understood as nucleic acids of any origin e.g. nucleic acids of viroid, viral, bacterial or cellular origin. If the nucleic acids in the sample are not readily accessible, they are preferably made accessible with appropriate reagents. This includes changing the pH (alkaline), heat, repeated extreme changes in temperature (freezing/thawing), changing the physiological growth conditions (osmotic pressure), action of detergents, chaotropic salts or enzymes (e.g. proteases and lipases). Sample material from which nucleic acids can be released in this manner are in particular cell-containing media, cell smears and tissue sections. The nucleic acids can be RNA as well as DNA.

Suitable vessels are in particular plastic vessels. Such vessels are for example made of polystyrene, polyethylene or luran. These have the advantage that they are easy to manufacture in a multiple injection moulding process while at the same time having a high mechanical stability under the conditions of the isolation method according to the invention.

Firstly the sample is taken up into a first vessel. For this purpose this vessel has a volume which allows the uptake of the entire sample and optionally of other reagents e.g. to facilitate binding of the nucleic acids to the nucleic-acid-binding material. The volume is preferably between 1 and 100 ml, preferably between 5 and 50 ml. This vessel preferably has an essentially cylindrical basic shape which is closed on one side. An opening is located on the other side of the vessel which is suitable for taking up the sample. In addition this vessel has means for attaching the vessel to a closing element preferably in the area near to the opening. This means can for example be an outer or inner screw thread. The vessel preferably has an additional opening (e.g. a pressure equalization opening). After the sample has been taken up into the first vessel, the sample is present in the first vessel but is not in contact with the nucleic-acid-binding material.

An additional important element of the invention is a closing element which contains the nucleic-acid-binding, liquid-permeable material. The nucleic-acid-binding material is arranged in the closing element such that sample liquid passing from the first vessel into the second vessel must pass through the nucleic-acid-binding material. In this process the nucleic acids are bound to the material. Hence the closing element connects the opening of the first vessel to the opening of a second vessel and the nucleic-acid-binding material is located between these openings. On one side of the nucleic-acid-binding material the closing element has means for attaching the element onto the first vessel. This means depends on the geometry of the first vessel in the area of the opening. If the first vessel for example has a thread, the means of the closing element is thus a matching counter-thread. The side of the closing element facing away from the opening of the first vessel has means for attaching the closing element to a second vessel. It has proven to be advantageous to also provide a screw thread here.

The design as well as the material of the second vessel can be similar to that of the first vessel. However, the second vessel should in particular be able to hold at least the volume of the sample liquid. The size of the second vessel is preferably equal to that of the first vessel or it has a volume which is that much larger than that of the first vessel that it can additionally hold wash liquid in addition to the sample liquid.

The closing element can be manufactured from the same material as the vessels, in this case the use of injection mouldable plastics is particularly preferred because these allow the liquid-permeable material to be introduced during the manufacture of the closing element. Especially in the case of glass fibre fleeces, the material can be permanently embedded in the closing element during the injection moulding process. It is however, also possible to introduce the material later and fasten it in the closing element e.g. by glueing or welding.

The closing element can comprise additional advantageous elements e.g. a connecting piece for applying underpressure. This connecting piece is preferably located on the side of the closing element which faces the second vessel.

In addition the closing element can contain a pressure equilibration connector. This is preferably in the part of the closing element that faces the first vessel or the side facing away from the suction connector. It is preferably designed such that under normal conditions no sample liquid can escape through it into the environment. It can for example be an opening closed by a dense fleece in the immediate vicinity of the nucleic-acid-binding material. Furthermore the closing element can also contain components which ensure a controlled and uniform flow through the nucleic-acid-binding material. This includes in particular a distribution of the stream of liquid over the entire available surface of the material as well as the collection of the stream of liquid when it enters the second vessel to prevent splashing of the liquid and a possible loss through the suction connector.

A system that is already very well suited for carrying out the method according to the invention is based on the component of the commercially available Steriflip™ vacuum filtration system from the Millipore Company in which, however, a glass fibre fleece is used instead of a sterile filtration membrane. A preferred embodiment of the method according to the invention based on this device is described in the following. 5 to 30 ml whole blood is pipetted into the first vessel. The cells should be lysed and disrupted in a first step. For this the necessary reagents e.g. a chaotropic salt or/and protease are added to the sample liquid. The first vessel is preferably tightly sealed with a cap and mixed. Afterwards the cap is removed and the closing element according to the invention is screwed on. The second vessel is either already attached to the closing element or it is subsequently attached to the closing element on the side of the nucleic-acid-binding material that faces away from the opening of the first vessel. Subsequently the sample liquid is passed through the nucleic-acid-binding material. This can, on the one hand, be carried out by tipping the assembled device (first vessel, closing element, second vessel) or be facilitated by additionally applying underpressure to the connector of the closing element. During passage of the sample liquid through the nucleic-acid-binding material, nucleic acids present in the sample that are now accessible are bound to the nucleic-acid-binding material while other sample components together with the liquid pass into the second vessel. Air from outside can enter into the first vessel through the second connector and thus equilibrate the underpressure formed in the first vessel. Hence the isolated nucleic acids are now located in the closing element bound to the liquid-permeable material. They can now be further processed in any desired manner.

Since certain amounts of sample liquid usually still adhere to the liquid-permeable material even after air has been sucked through, it is preferable to wash off these adhering residues. For this purpose the first vessel can for example be separated from the first closing element e.g. it is unscrewed and the wash liquid is applied to the material to which the nucleic acids are bound i.e. it is added dropwise. If a larger amount of wash liquid is used, it is also possible to attach a filler connection with the aid of the means used to attach the first vessel to the closing element. The wash liquid can be sucked through the material into the second vessel by applying underpressure. If it is intended to detach the nucleic acids from the liquid-permeable material, the second vessel can be removed from the closing element and replaced by a fresh third vessel. The third vessel can be attached with the aid of the means for attaching the second vessel to the closing element. Subsequently an elution liquid is applied preferably to the side on which the first vessel was attached and, if desired, is sucked through the material into the third vessel using underpressure. The elution liquid is designed such that it abolishes the binding of the nucleic acids to the liquid-permeable material. It is now possible to dissolve the nucleic acids in very small volumes of elution liquid. Hence the third vessel can also have a smaller volume than the second and first vessel. Thus the device according to the invention is also suitable for transferring nucleic acids from a larger volume into a smaller volume in addition to isolating nucleic acids.

FIG. 1A shows a closing element (1) which has a first screw thread (2) as well as a second screw thread (7). A pressure equilibration connector (8) is provided on the side of the screw thread (2) which is sealed air-tight but not liquid-impermeable by a dense fleece. A suction port for underpressure (3) and a splash protection (5) are located on the side of the second screw thread. The nucleic-acid-binding material (4) is located between the screw threads.

FIG. 1B shows a first vessel (10) with a counter-thread for the screw thread (2) (11) and a sample liquid (12) containing nucleic acid.

In FIG. 1C the closing element (1) is screwed onto the first vessel containing the sample liquid in such a way that the suction port (3) is separated from the sample liquid by the material (4). The second vessel (20) with a counter thread for the screw thread (7) (21) is shown.

Figure 1D:
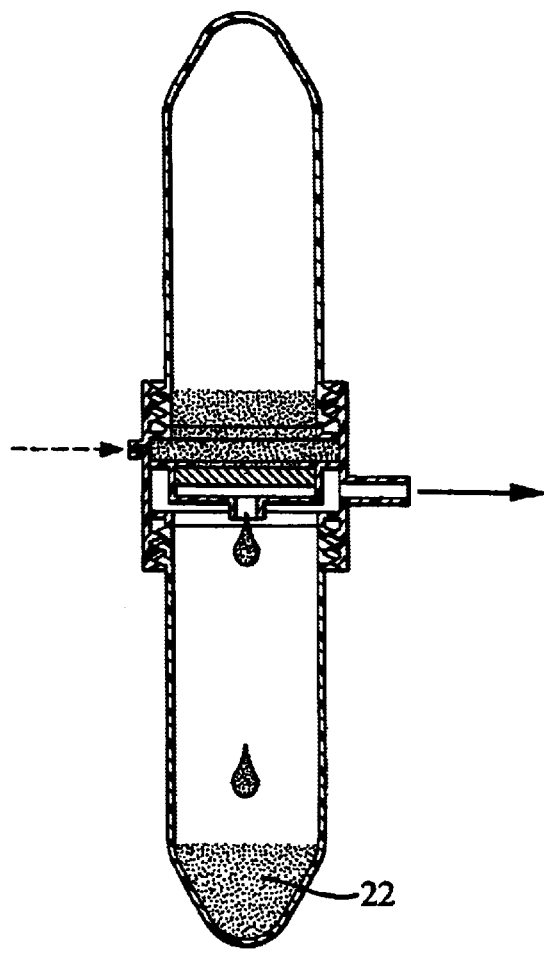

FIG. 1D shows the assembled device in a state in which underpressure has already been applied and part of the sample liquid has passed through the nucleic-acid-binding material (4). The liquid (22) that has passed through collects in the second vessel (20). It can be seen that the device was turned around (FIG. 1D) after unscrewing the second vessel (see FIG. 1C).

The invention also concerns a device for isolating nucleic acids from a sample comprising a first vessel capable of holding the sample with an opening and a closing element with a nucleic-acid-binding, liquid-permeable material wherein the closing element has means for attaching the element to a second vessel on the side facing away from the first vessel. The connection between the first vessel and the closing element should be so tight that no liquid can penetrate outside and no gas can penetrate inside between the closing element and the first vessel.

An additional subject matter of the invention is the use of a device with a first and a second vessel and a closing element for firmly connecting these vessels which contains a nucleic-acid-binding material to avoid contamination when preparing samples for nucleic acid tests. The nucleic acids eluted after the isolation from the liquid-permeable material can be used in an advantageous manner to detect individual nucleic acids or several of these nucleic acids from the sample. Appropriate detection methods are known to a person skilled in the art. They comprise in particular the amplification of the isolated nucleic acids and their detection using labelled nucleic acid probes.

The described method allows the simple isolation of nucleic acids from relatively large sample volumes ($\geq 10$ ml) with a reduced risk of contaminating the sample, the operator and the work place. The spread of aerosols is prevented by the arrangement of sample vessels and the filtration unit. The lysis and further processing of the sample can conveniently take place at a separate time and place without requiring a change of vessels (e.g. de-central sample withdrawal and lysis/stabilization).

The following example is intended to further elucidate the present invention.

EXAMPLE

It is intended to describe the present invention using a nucleic acid analysis from 20 ml whole blood as an example e.g. a test for the 9:22 translocation in leukaemias or prostate membrane antigen (PMA) based on the tumour-associated gene expression by reverse tranceriptase PCR (RT-PCR). FIG. 1 serves as an illustration.

All operations are carried out under the usual laboratory conditions for handling potentially pathogenic human material. 10 ml lysis buffer (6 M guanidinium HCl, 10 mM urea, 10 mM Tris-HCl, 20% Triton X-100 (v/v), pH 4.4 (25° C.) is added to 10 ml whole blood in a 50 ml polypropylene vessel (Millipore SC50 TB1 00). 2 ml of a proteinase K solution (20 mg/ml, Boehringer Mannheim, Cat. No. 1000 144) is added, the vessel is closed and immediately mixed thoroughly on a vortex mixer. It is subsequently incubated for 10 minutes at 70° C. The vessel is cooled, briefly centrifuged (Heraeus Sepatech Varifuge 3.0R), opened and 5 ml i-propanol is added and mixed well. A Steriflip™ (Millipore) filtration unit which contains two layers of glass fleece (e.g. Gelman S80100 A/E glass fibre, S80352 A/F glass fibre, S80348 A/C glass fibre, S80038 extra thick glass fibre, glued or welded) instead of the Millipore Express™ membrane is screwed onto the thread of the cap.

The outlet of the filtration unit carries an additional 50 ml sample vessel on the side of the glass fleece facing away from the first vessel which can be placed under underpressure via a connection located on the filtration unit. Such a sample vessel can for example be taken from the Steriflip™ filter unit (Millipore, cat. No. SCGP 005 25). The assembled unit is now oriented (e.g. rotated) such that the lysed sample material is located in the upper container and a vacuum is applied (e.g. water jet vacuum). The vacuum line is usually protected from contamination by an appropriate filter (e.g. Millipore Cat. No. SLFG 050 10). When the sample passes through the glass fleece, nucleic acids are bound to the surface of the glass fleece while most of the proteins, lipids and other components of the sample material pass through the fleece (eluate). Now the upper (first) vessel is removed and replaced by a cylinder (e.g. Millipore steriflip funnel top cat. No. SC05 FLO 25). Now 2×10 ml of a wash buffer (20 ml NaCl, 2 mM Tris-HCl, 80% ethanol (v/v), pH 7.5 (25° C.) is sucked through the glass fleece when a vacuum is applied. Finally the cylinder is replaced by a cap and the unit is centrifuged in order to remove residual wash buffer from the glass fleece. Alternatively the fleece can also be dried by sucking sterile air through it. The vessel containing the eluate is now removed and replaced by a fresh sterile vessel. 1–2 ml elution buffer (10 mM Tris-HCl, pH 8.5) preheated to 70° C. is applied to the fleece and sucked through with a vacuum. In order to obtain an optimal yield, the unit is subsequently centrifuged at ca. 8000×g. The isolated nucleic acid is located in the eluate and contains DNA as well as RNA and is now suitable for use in PCR or RT-PCR.

List of Reference Numerals 1 closing element
2 first screw thread
3 suction port for underpressure
4 nucleic-acid-binding material (fleece)
5 splash protection
6 stop for screw thread
7 second screw thread
8 pressure equilibration port
10 first vessel
11 counter-thread for 2
12 sample liquid containing nucleic acid
20 second vessel
21 counter-thread for 7
22 liquid that has passed through

What is claimed is:

1. A method for isolating nucleic acids from a sample, comprising:

a) taking the sample into a first vessel through an opening in the first vessel, b) closing the opening in the first vessel with a closing element, wherein the closing element comprises a glass fleece or a membrane comprising metal oxides, metal mixed oxides, silica gel, aluminum oxide, zeolite, titanium oxide or zirconium oxide, in the form of fibres or particles, on a side facing the opening, means for attaching the element on the first vessel and, on an other side, means for attaching the element to a second vessel, and c) transferring the sample through the material into a second vessel wherein the second vessel is attached on the other side of the closing element, and wherein the sample is transferred by applying an underpressure in the second vessel;

wherein said glass fleece or membrane is not functionalized with ion-exchange substituents.

2. A method as claimed in claim 1, wherein the sample comprises cells, and the method further comprises, after taking the sample into the first vessel, releasing nucleic acids from the cells by lysis.

3. A method as claimed in claim 1, further comprising:

d) eluting nucleic acids from the nucleic-acid-binding material.

4. A method as claimed in claim 1, further comprising:

contacting the sample in the first vessel with the material by rotating the first vessel before transferring the sample through the material.

5. A method as claimed in claim 1, wherein the first vessel has a volume of more than 5 ml.

6. A method as claimed in claim 2, further comprising:

d) eluting nucleic acids from the nucleic-acid-binding material.

7. A method as claimed in claim 2, further comprising:

contacting the sample in the first vessel with the material by rotating the first vessel before transferring the sample through the material.

8. A method as claimed in claim 3, further comprising:

contacting the sample in the first vessel with the material by rotating the first vessel before transferring the sample through the material.

9. A method as claimed in claim 2, wherein the first vessel has a volume of more than 5 ml.

10. A method as claimed in claim 3, wherein the first vessel has a volume of more than 5 ml.

11. A method as claimed in claim 4, wherein the first vessel has a volume of more than 5 ml.

* * * * *